US008597369B2

(12) United States Patent
Hansen et al.

(10) Patent No.: US 8,597,369 B2
(45) Date of Patent: Dec. 3, 2013

(54) EQUILIBRIUM-POINT PROSTHETIC AND ORTHOTIC ANKLE-FOOT SYSTEMS AND DEVICES

(75) Inventors: Andrew H. Hansen, Round Lake, IL (US); Steven A. Gard, Naperville, IL (US); Dudley S. Childress, Wilmette, IL (US); Brian Ruhe, Chicago, IL (US); Ryan Williams, Albuquerque, NM (US)

(73) Assignees: Northwestern University, Evanston, IL (US); The Department of Veteran Affairs, Washington, DC (US); The Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 12/311,818

(22) PCT Filed: Oct. 17, 2007

(86) PCT No.: PCT/US2007/022208
§ 371 (c)(1),
(2), (4) Date: Apr. 13, 2009

(87) PCT Pub. No.: WO2008/048658
PCT Pub. Date: Apr. 28, 2008

(65) Prior Publication Data
US 2010/0185301 A1 Jul. 22, 2010

Related U.S. Application Data

(60) Provisional application No. 60/852,174, filed on Oct. 17, 2006.

(51) Int. Cl.
*A61F 2/66* (2006.01)

(52) U.S. Cl.
USPC .................................. 623/50; 623/53; 623/47

(58) Field of Classification Search
USPC .......................................... 623/24–27, 47–56
See application file for complete search history.

(56) References Cited

U.S. PATENT DOCUMENTS

| | | | | |
|---|---|---|---|---|
| 1,951,622 A | * | 3/1934 | McElroy | 623/43 |
| 4,360,931 A | | 11/1982 | Hampton | |
| 4,413,360 A | | 11/1983 | Lamb | |
| 4,547,913 A | | 10/1985 | Phillips | |
| 4,555,817 A | | 12/1985 | McKendrick | |
| 6,007,582 A | * | 12/1999 | May | 623/55 |
| 6,159,248 A | | 12/2000 | Gramnas | |
| 6,217,249 B1 | | 4/2001 | Merlo | |
| 6,436,149 B1 | | 8/2002 | Rincoe | |
| 6,443,993 B1 | | 9/2002 | Koniuk | |
| 6,500,138 B1 | * | 12/2002 | Irby et al. | 602/26 |

(Continued)

OTHER PUBLICATIONS

Feldman, Once More on the Equilibrium-point Hypothesis (lambda model) for Motor Control, J. Motor Behav., 18, 1986, pp. 17-54.

(Continued)

*Primary Examiner* — David Isabella
*Assistant Examiner* — Marcia Hoffman
(74) *Attorney, Agent, or Firm* — Cook Alex Ltd.

(57) ABSTRACT

The present invention relates to a system for use in rehabilitation and/or physical therapy for the treatment of injury or disease. The system can enable an amputee to proceed over any surface without overbalancing. In particular the system is self-adapting to adjust the torque moment depending upon the motion, the extent of inclination, and the surface topography.

9 Claims, 11 Drawing Sheets

(56) References Cited

U.S. PATENT DOCUMENTS

| | | | |
|---|---|---|---|
| 7,431,737 B2 | 10/2008 | Ragnarsdottir et al. | |
| 2004/0064195 A1* | 4/2004 | Herr | 623/24 |
| 2004/0153168 A1 | 8/2004 | Childress et al. | |
| 2005/0192677 A1 | 9/2005 | Ragnarsdottir | |
| 2005/0197717 A1* | 9/2005 | Ragnarsdottir et al. | 623/24 |
| 2006/0184280 A1 | 8/2006 | Oddsson | |
| 2006/0224246 A1* | 10/2006 | Clausen et al. | 623/24 |
| 2006/0224247 A1 | 10/2006 | Clausen | |
| 2006/0249315 A1* | 11/2006 | Herr et al. | 180/8.1 |
| 2007/0043449 A1* | 2/2007 | Herr et al. | 623/24 |
| 2007/0061016 A1* | 3/2007 | Kuo et al. | 623/24 |
| 2009/0319055 A1* | 12/2009 | Iversen et al. | 623/49 |

OTHER PUBLICATIONS

Perry, Gait Analysis: Normal and Pathological Function, 1992, Slack Inc., 1992.

Latash et al., Joint Stiffness: Myth or Reality?; Hum. Mov. Sci, 12, 1993, pp. 653-692.

Irby et al., Optimization and Application of a Wrap-Spring Clutch to a Dynamic Knee-Ankle-Foot Orthosis, IEEE Trans. Rehabll. Eng., 7, 2, 1999, pp. 130-134.

Ferris et al., Runners Adjust Leg Stiffness for Their First Step on a New Running Surface; J. Biomech.; 32, 8, pp. 787-794, 1999.

Hansen, Roll-over Characteristics of Human Walking With Applications for Artificial Limbs; Dissertation, 2002.

Leroux et al., Postural Adaptations to Walking on Inclined Surfaces: I. Normal Strategies, Gait & Pos., 15, 1, 2002, pp. 67-74.

Hansen et al., The Human Ankle During Walking: Implications for Design of Biomimetic Ankle Prostheses, J. Biomech; 37, 10, pp. 1467-1474.

Hansen et al., Roll-over Characteristics of Human Walking on Inclined Surfaces; Hum, Mov. Sci.; 23, 6, pp. 807-821.

Prentice et al., Locomotor Adaptations for Changes in Slope of the Walking Surface; Gait & Pos.; 20, 3, pp. 255-265.

Lay, The Effects of Sloped Surfaces on Locomotion: A Kinematic and Kinetic Analysis, J. Biomech., 39, 9, 2006, pp. 1621-1628.

Williams et al., Prosthetic Ankle-Foot Mechanism Capable of Automatic Adaptation to the Walking Surface; J. Biomech. Eng., 131, 3, 2009.

PCT/US2007/022208 International Search Report.

PCT/US2007/022208 Written Opinion of the International Search Authority.

PCT/US2011/000675 International Search Report.

PCT/US2011/000675 Written Opinion of the International Search Authority.

PCT/US2012/000038 International Search Report.

* cited by examiner

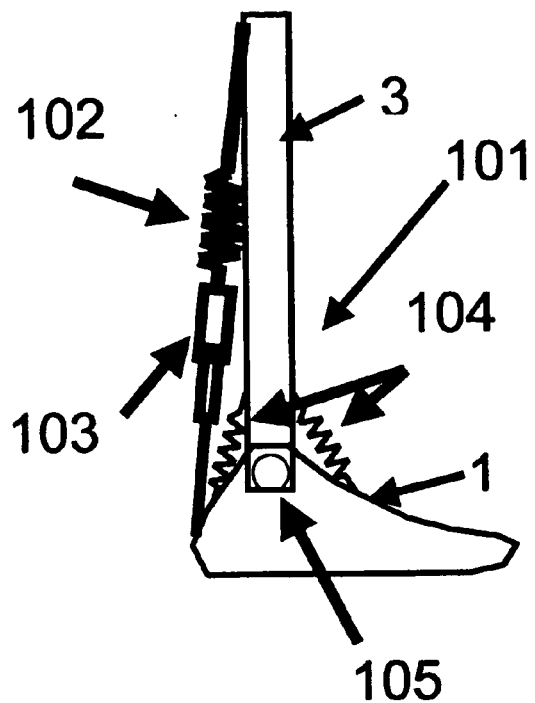 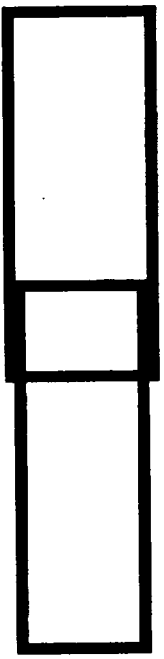 
Fig 1    Fig 2A    Fig 2B
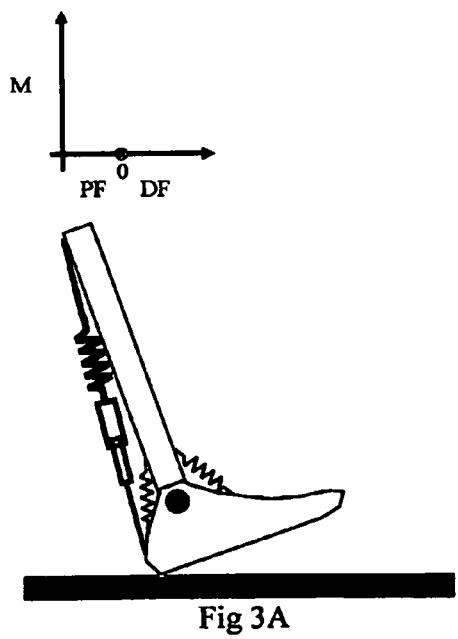 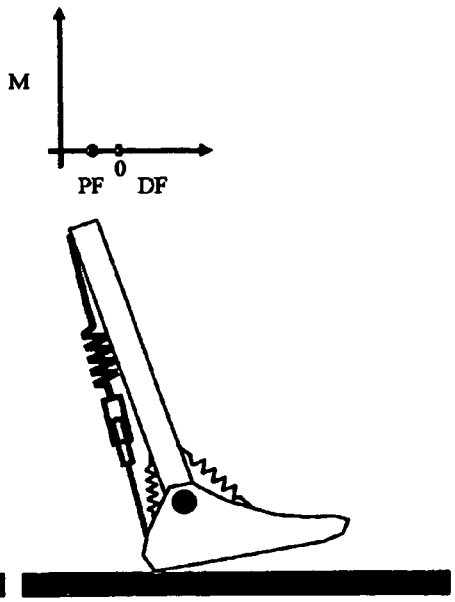
Fig 3A    Fig 3B

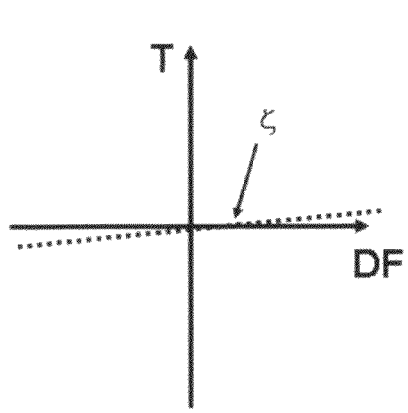
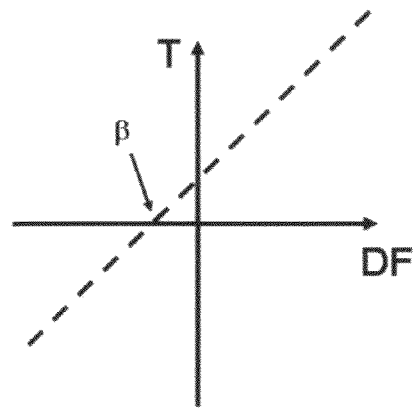
PRIOR ART
Fig 4
Fig 5
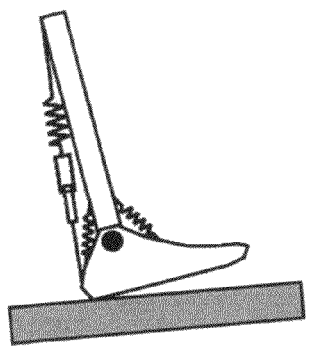
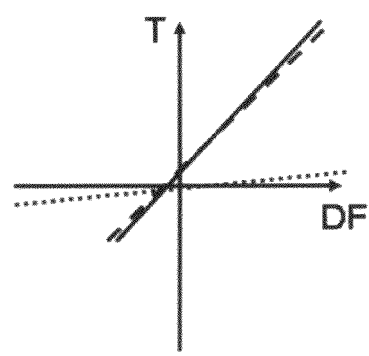
Fig 6A
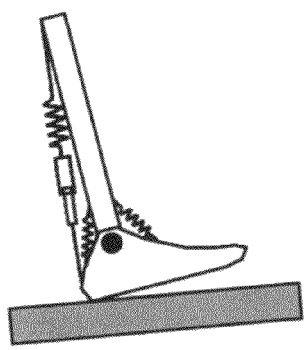
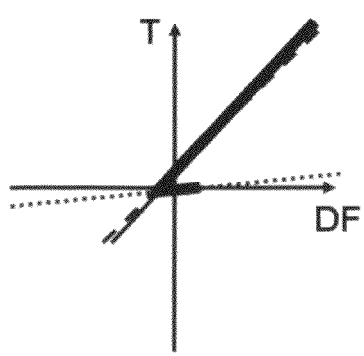
Fig 6B

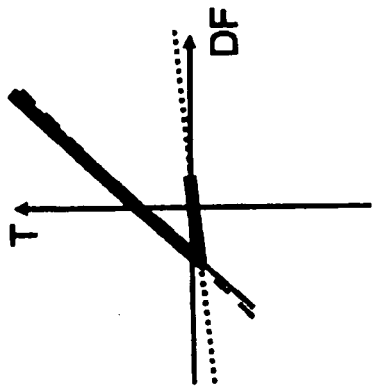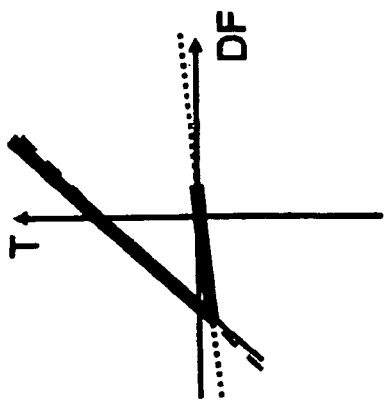
Fig 6C  Fig 6D
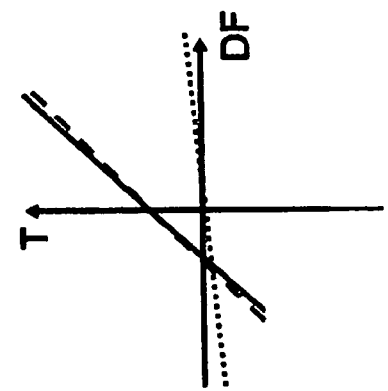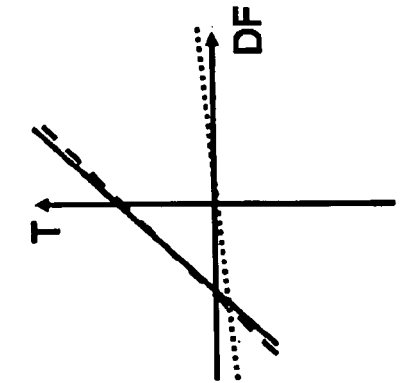
Fig 6E  Fig 6F
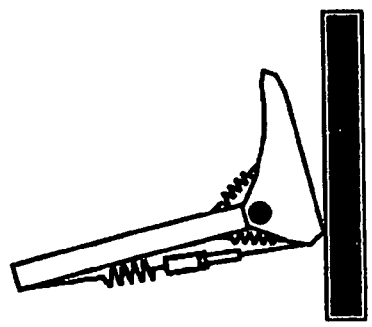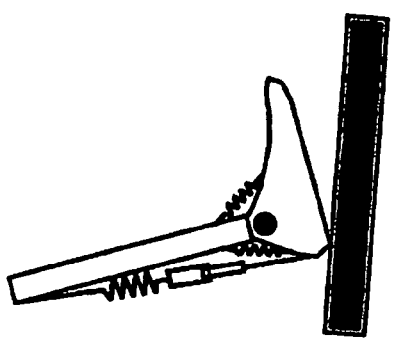
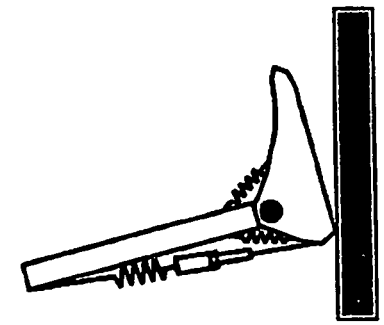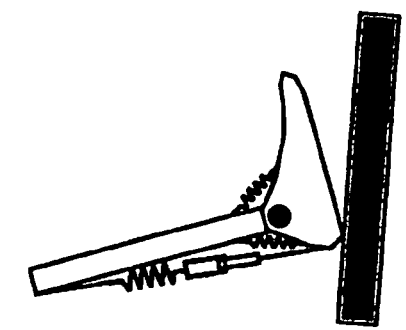

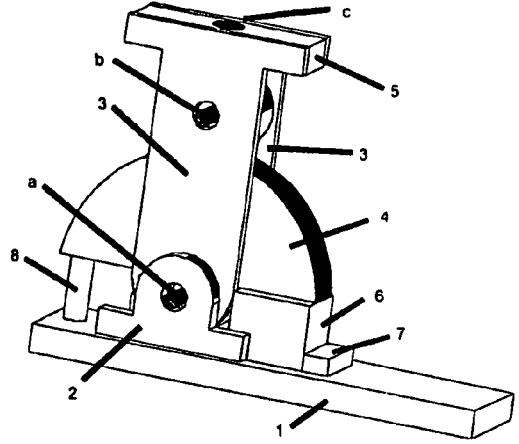
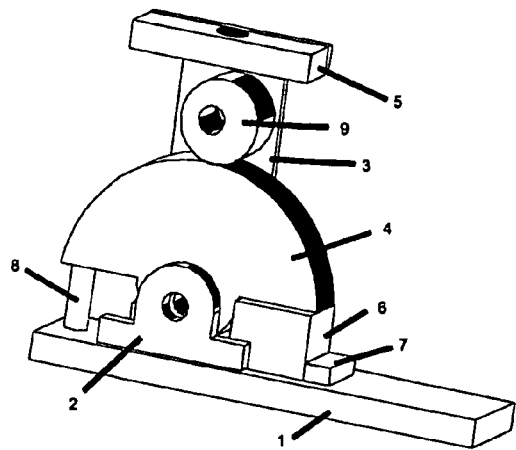
Fig 9A　　　　　　　　　　　Fig 9B
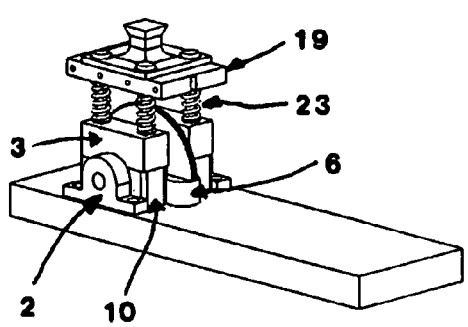
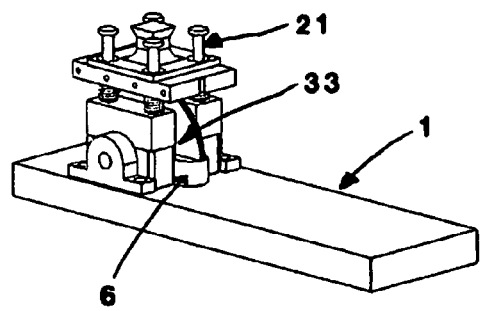
Fig 10A　　　　　　　　　　Fig 10B
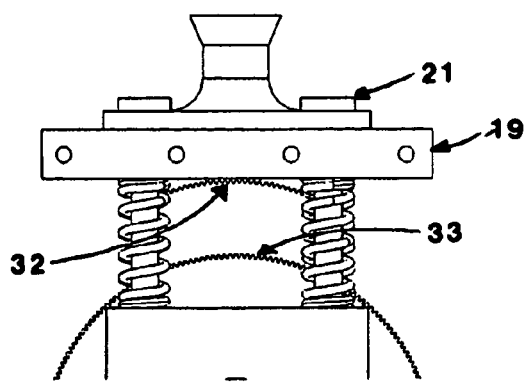
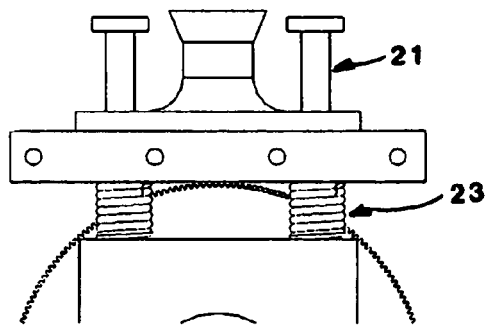
Fig 11A　　　　　　　　　　Fig 11B

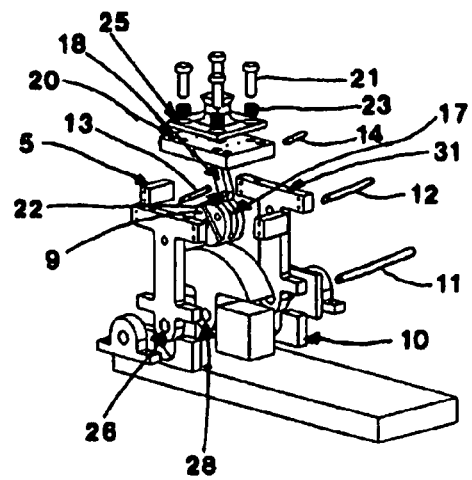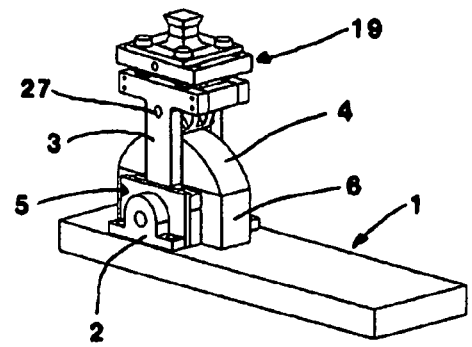
Fig 12A   Fig 12B
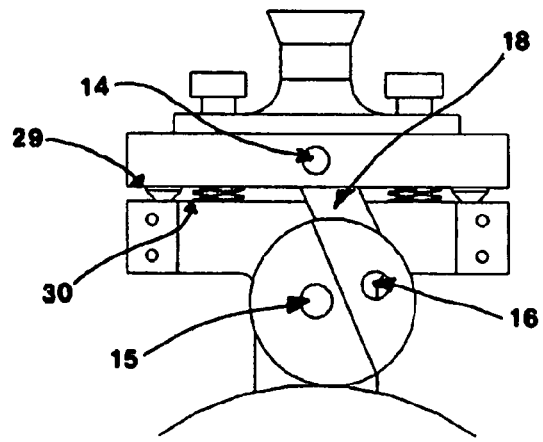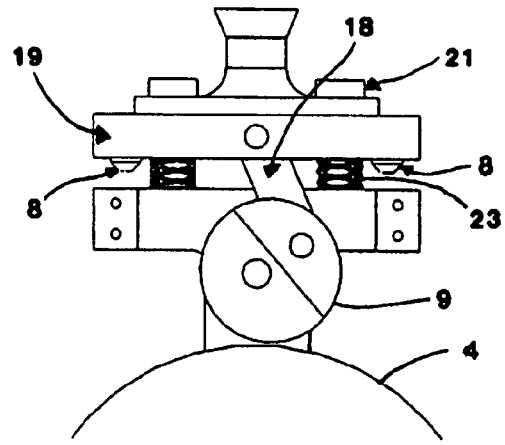
Fig 13A   Fig 13B

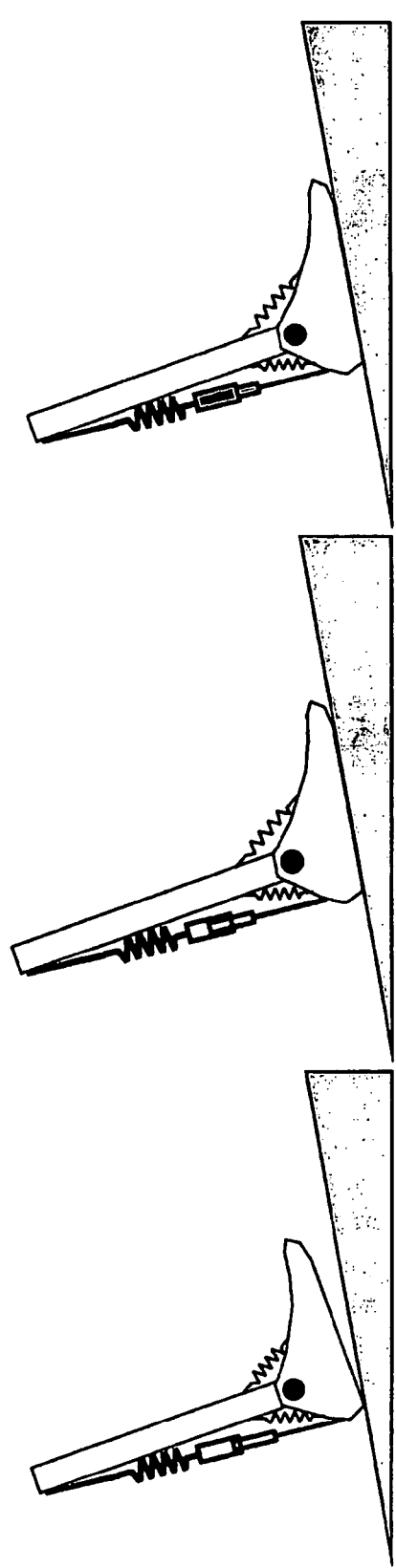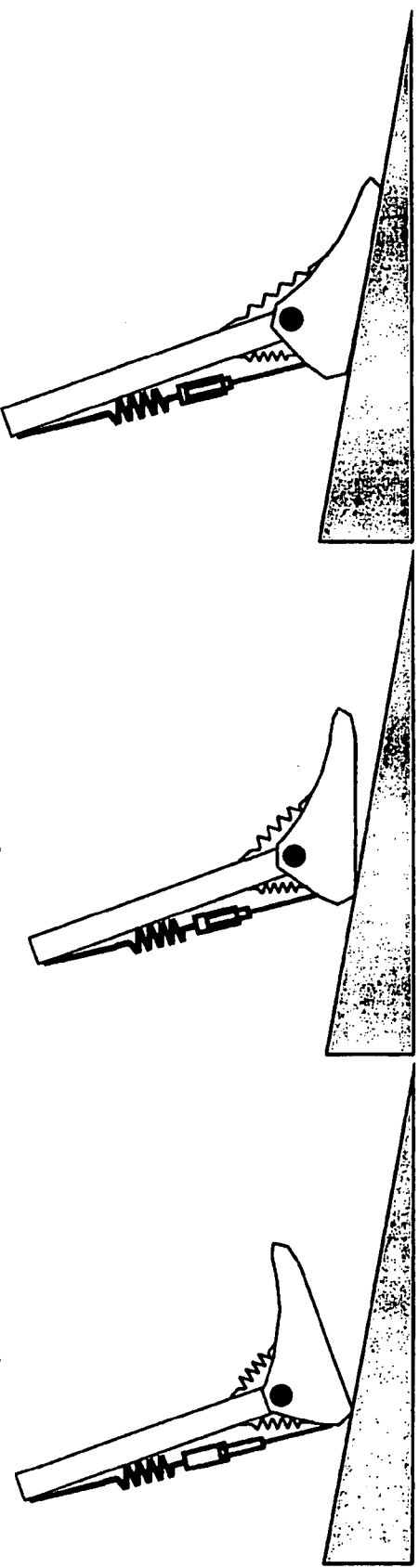

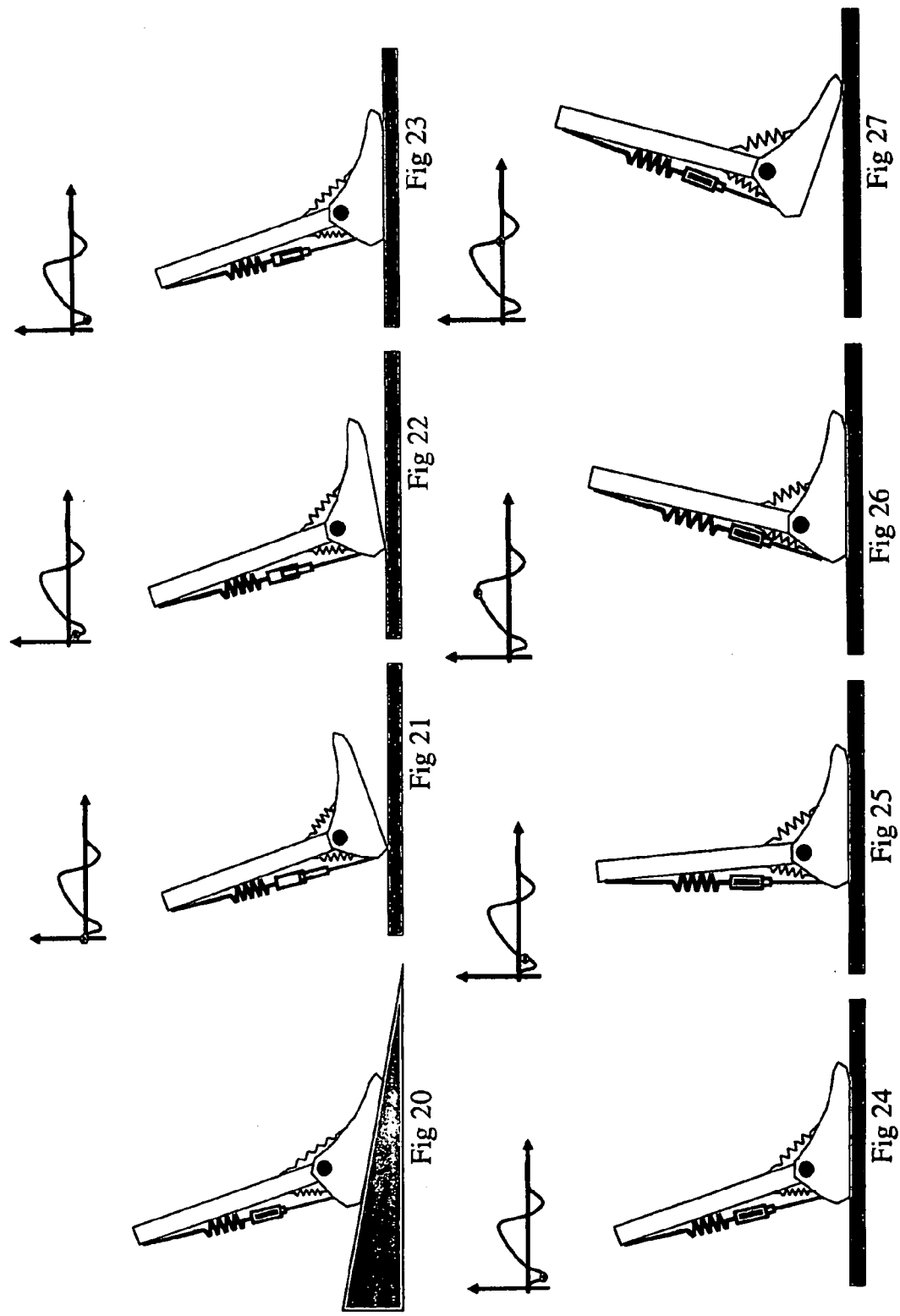

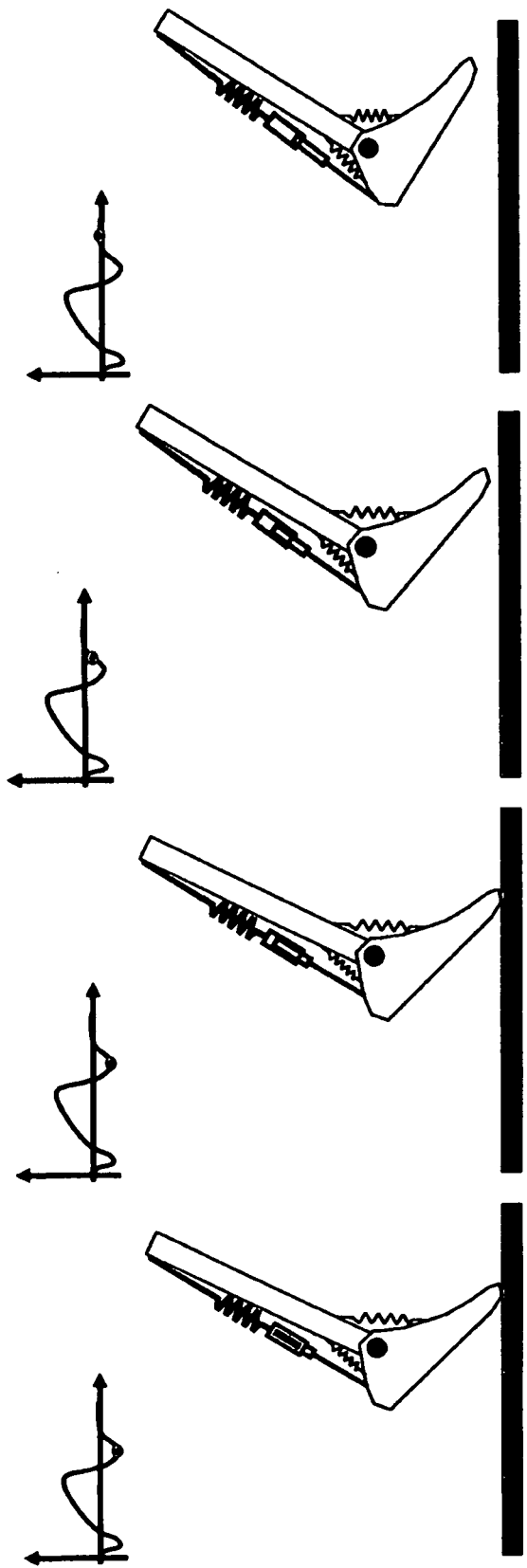

US 8,597,369 B2

EQUILIBRIUM-POINT PROSTHETIC AND ORTHOTIC ANKLE-FOOT SYSTEMS AND DEVICES

CROSS-REFERENCE TO RELATED APPLICATIONS

The present application claims priority to International Patent Application Number PCT/US07/22208 entitled "Equilibrium-Point Prosthetic and Orthotic Ankle-Foot Systems, Devices, and Methods of Use", filed Oct. 17, 2007, which in turn claimed priority to U.S. Provisional Patent Application Ser. No. 60/852,174 entitled "Equilibrium-Point Prosthetic and Orthotic Ankle-Foot Devices", filed Oct. 17, 2006, both which are herein incorporated by reference in their entirety for all purposes.

STATEMENT REGARDING FEDERALLY SPONSORED RESEARCH OR DEVELOPMENT

This invention was made with government support under H133E030030 awarded by the National Institute on Disability and Rehabilitation Research (United States Department of Education). The United States government has certain rights in the invention.

TECHNICAL FIELD

The inventions relates to improved prosthetic systems and methods of use. In particular the prosthesic systems comprise an ankle unit that, in combination with other mechanical elements of prosthesic systems, enable the gait of an amputee using the device to emulate the gait of able-bodied individual and that automatically adapts the gait to different terrain on each and every step.

BACKGROUND OF THE INVENTION

Many currently available prosthetic and orthotic ankle-foot mechanisms do not allow ankle motion. Rigid ankle prosthetic and orthotic ankle-foot devices generally attempt to replace the actions of the biologic ankle-foot system through deformations of their materials and/or by utilizing rocker shapes on the plantar surfaces. The prosthetic and orthotic ankle-foot devices that do incorporate ankle motion usually allow rotational motion about a single point that does not change without mechanical adjustments of the prosthesis or orthosis. Some of these devices use springs and/or bumpers to store and release energy and return the device's ankle joint to one "equilibrium" point. This single and constant "equilibrium" point can result in good function on level terrain and when using shoes of one particular heel height (heel and forefoot sole differential). However, problems can arise when walking on different terrain or when using shoes of different heel height. The heel height problem can be fixed using a change in the alignment of the prosthesis. However, this is not a simple task and one that does not happen automatically.

A recent patent issued to Wayne Koniuk (U.S. Pat. No. 6,443,993 B1, "Self-Adjusting Prosthetic Ankle Apparatus", issued Sep. 3, 2002) discloses a device that will adapt to various terrains and to shoes of different heel height. However, Koniuk's design does not appear to have energy storage and release properties, utilizes more sensing devices than the proposed design, and does not appear to give plantarflexion at late stance. Koniuk's design is based on damping control of the ankle joint whereas the proposed device is based on the control of stiffness about the ankle. Damping removes energy from a system whereas stiffness can store and release energy to a system throughout a loading and unloading cycle (that is, a walking cycle).

Recent research has suggested that roll-over shape, the effective rocker shape that the ankle-foot system conforms to between heel contact and opposite heel contact, is an important characteristic for walking. Hansen ((2002); "Roll-over Characteristics of Human Walking With Applications for Artificial Limbs." Ph.D. dissertation, Northwestern University, Evanston, Ill.) found that the able-bodied ankle-foot system adapts to several walking conditions to maintain a similar roll-over shape and that its roll-over shape changes predictably when walking on inclined surfaces. Specifically, able-bodied ankle-foot systems are capable of automatically adapting to differences in shoe heel height and to different surface inclinations. Current prosthetic ankle-foot mechanisms cannot automatically adapt to these conditions. Many currently available prosthetic and orthotic ankle-foot mechanisms do not allow ankle motion. Rigid ankle prosthetic and orthotic ankle-foot devices generally attempt to replace the actions of the biologic ankle-foot system through deformations of their materials and/or by utilizing rocker shapes on the plantar surfaces. The prosthetic and orthotic ankle-foot devices that do incorporate ankle motion usually allow rotational motion about one equilibrium point that does not change without mechanical adjustments of the prosthesis or orthosis. Some of these devices use springs and/or bumpers to store and release energy and return the device's ankle joint to one equilibrium point. This single and constant equilibrium point can result in good function on level terrain and when using shoes of one particular heel height (heel and forefoot sole differential). However, problems can arise when walking on different terrain or when using shoes of different heel height. The heel height problem can be fixed using a change in the alignment of the prosthesis. However, this is not a simple task and one that does not happen automatically.

The prior art demonstrates that there is a current and long-felt need for an improved ankle prosthesis or ankle-foot prosthesis that can better emulate the gait of an able-bodied individual and adapt to the terrain on the first step.

BRIEF SUMMARY OF THE INVENTION

The invention provides a prosthetic and orthotic ankle-foot device. The system can be used by a human subject as a prosthesis to assist the user's gait and to prevent or reduce the likelihood of compromising the user's balance.

In one embodiment the invention provides a prosthetic system for a user to emulate normal gait, the prosthetic system comprising an ankle member, the ankle member comprising a reversible engagement means, a first torsion means, and a joint, and wherein in use, a torsion curve plot of ankle moment against ankle dorsiflexion angle of the prosthetic system during a gait cycle comprises at least one transition point, wherein the reversible engagement means is operatively connected to the first torsion means, wherein the first torsion means is operatively connected to the joint, and wherein the joint is operatively connected to the engagement means. In a preferred embodiment the system is used by a user to proceed over a surface without compromising balance wherein the surface comprises a plurality of grades or elevations. More preferably the torsion curve plot comprises a plurality of transition points. In one alternative embodiment the transition point of the torsion curve plot is at a negative torque moment. In another alternative embodiment the transition point of the torsion curve plot is at a negative ankle dorsiflexion angle. In another alternative embodiment the transition point of the torsion curve plot is at a positive torque moment. In yet another alternative embodiment the transition point of the torsion curve plot is at a positive ankle dorsiflexion angle. In a most preferred embodiment the prosthetic system automatically adapts to different surface conditions.

In one embodiment the prosthetic system comprises a composition selected from the group consisting of stainless steel, copper, aluminum, titanium, metal matrix composite, metal alloy, such as NITINOL, DELRIN (acetal), acrylonitrile butadiene styrene (ABS), nylon, polypropylene, polybromate, polycarbonate, glycolised polyethylene terephthalate (PETg) copolyester, olytetrafluorethylene (PTFE), ePTFE, polypropylene, a polymer, glass fiber-resin composites, carbon fiber resin composites, and the like.

In a preferred embodiment the invention provides a prosthetic system as disclosed wherein the engagement means is selected from the group consisting of a lock, a piston, a ratchet, a clutch, a brake, and the like. In another preferred embodiment the torsion means is selected from the group consisting of a spring, a tunable spring, a clockwork spring, a piston, a damper, and the like In another embodiment the invention provides a prosthetic system as disclosed further comprising at least one second torsion means. Preferably, the second torsion means comprises a pair of neutralizing torsion means.

In one embodiment the invention provides the prosthetic system as disclosed further comprising a foot plate. In another embodiment the prosthetic system further comprises a shin member. In another embodiment the prosthetic system further comprises a microprocessor. In another embodiment the prosthetic system further comprises a motor. In another embodiment the prosthetic system further comprises an actuator. In another embodiment the prosthetic system further comprises a potentiometer.

The invention also provides a prosthetic system for a user to emulate normal gait, the prosthetic system comprising an ankle member, the ankle member comprising a reversible engagement means, torsion means, and a joint, and wherein in use, a torsion curve plot of ankle moment against ankle dorsiflexion angle of the prosthetic system during a gait cycle comprises at least two equilibrium points, wherein the reversible engagement means is operatively connected to the first torsion means, wherein the first torsion means is operatively connected to the joint, and wherein the joint is operatively connected to the engagement means. In a preferred embodiment the system is used by a user to proceed over a surface without overbalancing wherein the surface comprises a plurality of grades or elevations.

More preferably the torsion curve plot comprises a plurality of transition points. In one alternative embodiment the transition point of the torsion curve plot is at a negative torque moment. In another alternative embodiment the transition point of the torsion curve plot is at a negative ankle dorsiflexion angle. In another alternative embodiment the transition point of the torsion curve plot is at a positive torque moment. In yet another alternative embodiment the transition point of the torsion curve plot is at a positive ankle dorsiflexion angle.

In a preferred embodiment the invention provides a prosthetic system as disclosed wherein the engagement means is selected from the group consisting of a lock, a piston, a ratchet, a clutch, a brake, or the like. In another preferred embodiment the torsion means is selected from the group consisting of a spring, a tunable spring, a clockwork spring, a piston, or the like.

In another embodiment the invention provides a prosthetic system as disclosed further comprising at least one second torsion means. Preferably, the second torsion means comprises a pair of neutralizing torsion means.

In one embodiment the invention provides the prosthetic system as disclosed further comprising a foot plate. In another embodiment the prosthetic system further comprises a shin member. In another embodiment the prosthetic system further comprises a microprocessor. In another embodiment the prosthetic system further comprises a motor. In another embodiment the prosthetic system further comprises an actuator. In another embodiment the prosthetic system further comprises a potentiometer.

The invention also provides a prosthetic ankle-foot device for a user to emulate normal gait, the prosthetic ankle-foot device comprising an ankle member, the ankle member comprising a reversible engagement means, a first torsion means, and a joint, and wherein in use, a torsion curve plot of ankle moment against ankle dorsiflexion angle of the prosthetic ankle-foot device during a gait cycle comprises at least one transition point, wherein the reversible engagement means is operatively connected to the first torsion means, wherein the first torsion means is operatively connected to the joint, and wherein the joint is operatively connected to the engagement means. In a most preferred embodiment the prosthetic ankle-foot device automatically adapts to different surface conditions.

The invention also provides a prosthetic prosthetic ankle-foot device for a user to emulate normal gait, the prosthetic ankle-foot device comprising an ankle member, the ankle member comprising a reversible engagement means, torsion means, and a joint, and wherein in use, a torsion curve plot of ankle moment against ankle dorsiflexion angle of the prosthetic ankle-foot device during a gait cycle comprises at least two equilibrium points, wherein the reversible engagement means is operatively connected to the first torsion means, wherein the first torsion means is operatively connected to the joint, and wherein the joint is operatively connected to the engagement means.

The invention also provides a prosthetic prosthetic ankle-foot device for a user to emulate normal gait, the prosthetic ankle-foot device comprising an ankle member, the ankle member comprising a reversible engagement means, torsion means, and a joint, and wherein in use, a torsion curve plot of ankle moment against ankle dorsiflexion angle of the prosthetic ankle-foot device during a gait cycle comprises at least two equilibrium points and wherein at least one of the two equilibrium points set is based upon the step conditions. In a preferred embodiment, the step condition is selected from the group consisting of speed or velocity, slope of terrain, and evenness of surface. In the alternative, at least one of the equilibrium points set during the gait cycle.

The invention further provides a method for providing normal gait in an amputee, the amputee having lost a lower limb extremity, the method comprising (i) providing the prosthetic system as disclosed herein; (ii) attaching the prosthetic system to the lower limb of the amputee; (iii) allowing the amputee to ambulate for at least one gait cycle, the gait cycle comprising at least two phases of dorsiflexion over time, whereby a load applied during a first phase of dorsiflexion results in the engagement means engaging and damping movement of the engagement means, wherein during the first phase when the ankle dorsiflexion angle is at an ankle angle minimum the engagement means engages and dampens fully, and wherein during a second phase of dorsiflexion when the ankle dorsiflexion angle is at another ankle angle minimum the engagement means disengages and releases fully, the method resulting in providing normal gait to the amputee. In one preferred embodiment the gait cycle comprises at least three phases of ankle flexion. In another preferred embodiment, the engagement and dampening of the engagement means coincides with a first transition point of the torsion curve plot. In yet another preferred embodiment, the disengagement and release of the engagement means coincides with a second transition point of the torsion curve plot.

In an alternative embodiment, the invention provides the method of using the prosthetic system further comprising a step of determining an equilibrium point of a torsion curve plot wherein an equilibrium point of the torsion curve plot is at a negative dorsiflexion angle. In an alternative embodiment an equilibrium point of the torsion-curve plot is at a positive dorsiflexion angle.

In a still further embodiment the invention provides a method for providing normal gait in an amputee, the amputee having lost a lower limb extremity, the method comprising (i) providing the prosthetic ankle-foot device as disclosed herein; (ii) attaching the prosthetic ankle-foot device to the lower limb of the amputee; (iii) allowing the amputee to ambulate for at least one gait cycle, the gait cycle comprising at least two phases of dorsiflexion over time, whereby a load applied during a first phase of dorsiflexion results in the engagement means engaging and damping movement of the engagement means, wherein during the first phase when the ankle dorsiflexion angle is at an ankle angle minimum dorsiflexion the engagement means engages and dampens fully, and wherein during a second phase of dorsiflexion when the ankle dorsiflexion angle is at another ankle angle minimum dorsiflexion the engagement means disengages and releases fully, the method resulting in providing normal gait to the amputee. In one preferred embodiment the gait cycle comprises at least three phases of ankle flexion. In another preferred embodiment, the engagement and dampening of the engagement means coincides with a first transition point of the torsion curve plot. In yet another preferred embodiment, the disengagement and release of the engagement means coincides with a second transition point of the torsion curve plot.

In an alternative embodiment, the invention provides the method of using the prosthetic system further comprising a step of determining an equilibrium point of a torsion curve plot wherein an equilibrium point of the torsion curve plot is at a negative dorsiflexion angle. In an alternative embodiment an equilibrium point of the torsion curve plot is at a positive dorsiflexion angle.

In one preferred embodiment, the torsion means are selected from the group consisting of an elastic element, a spring, a piston, and the like.

In a more preferred embodiment, the equilibrium point $\beta$ of the torsion curve plot is calculated using the equation $$T_{ts}=k_{ts}(\theta-\beta),$$

where $T_{ts}$=torque due to triceps surae spring(s); $\theta$=ankle dorsiflexion angle; $\beta$=ankle angle at the trigger time; and $k_{ts}$ is the impedance factor. In an alternative more preferred embodiment the equilibrium point $\zeta$ of the torsion curve plot is calculated using the equation $$T_{ns}=k_{ns}(\theta-\zeta),$$

where $T_{ns}$=torque due to neutralizing spring(s); $\theta$=ankle dorsiflexion angle; $\zeta$=ankle dorsiflexion bias; and $k_{ns}$ is the impedance factor.

In another embodiment the invention provides a prosthetic ankle-foot device that emulates normal gait, the prosthetic device comprising, in combination, a reversible engagement (locking/unlocking) member, a foot member, an upper member, an ankle joint for connecting the foot member to the upper member, wherein the ankle joint further comprises a pair of arms, each arm having a first end and a second end, a pair of first bumpers, a pair of bearings, a pair of second bumpers, the second bumpers positioned longitudinally along the length of the foot member, a base, a first shaft, a second shaft, a third shaft, a fourth shaft a pair of braces, a cam, the cam having an off-center first aperture, and optionally, a cam allowing rotation in one direction but not the other, at least one second aperture, and a recess, the recess shaped and adapted to receive a link, the first aperture shaped and adapted for receiving a first shaft therethrough and wherein the first shaft can revolve therein, a housing, the housing having at least two threaded apertures shaped and adapted to receive a bolt, the link connected to the housing using a fourth shaft positioned through a first link aperture in the link and a least one aperture located in a flange abutting from the housing and having at least one second link aperture at the end of the link opposing the housing, at least two bolts, at least two compression springs, an adaptor, the adaptor having at least two bolt apertures shaped and adapted for receiving a bolt therethrough, at least two set screws, wherein the arm has a first apertures located at the first end and a second aperture located at the second end, the apertures sized and spaced to receive a second shaft therethrough and wherein the second shaft can revolve therein, wherein the base has at least one aperture, the aperture sized and spaced to receive the second shaft therethrough, wherein the bearings are in lateral opposition fixedly attached to the foot member, the first end of the arms positioned between the two bearings and in contact with the first bumpers, the first bumpers secured to the foot member and supporting the arms, the base centered between the two bearings and in contact with the second bumpers, wherein the braces are positioned and secured between the second end of the arms, wherein the cam is centered between the second end of each arm and having a surface in intermittent contact with a surface of the base, the surface contact dependent upon the rotated position of the cam, wherein the link aperture is positioned in-line with the second aperture of the cam and a third shaft positioned therethough and wherein the third shaft can revolve therein, wherein the adaptor is positioned proximal to the housing, wherein each bolt is positioned through an aperture in the adaptor and is threaded into a threaded aperture in the housing, wherein each compression spring is placed longitudinally encircling the bolt thread between the bolt head and the adaptor, and the bolt is reversibly threaded through the housing bolt aperture and into a threaded recess in the second end of the arm. In one embodiment second bumper is substantially stiff. In an alternative embodiment the first bumper is substantially soft. In an alternative embodiment the prosthetic foot further comprises a pair of spacers, the spacer shaped and adapted for placement between a bearing and an arm.

In a preferred embodiment the prosthetic ankle-foot device has a plurality of equilibrium points, when used as disclosed herein.

In another preferred embodiment the prosthetic ankle-foot has a plurality of transition points, when used as disclosed herein. In one embodiment the relative position of the transition point can be controlled, such as for example, by a microprocessor, a motor, an actuator, by the user, a force generator, a force sensor, or the like.

In an alternative embodiment the invention provides a prosthetic foot and ankle device that emulates normal gait, the prosthetic foot and ankle device comprising, in combination, a foot member, a shank member, an ankle joint for connecting the foot member to the shank member, a brake, a microprocessor, an angular encoder, wherein the ankle joint further comprises a pair of arms, each arm having a first end and a second end, a pair of soft bumpers, a pair of bearings, a pair of stiff bumpers, the stiff bumpers positioned longitudinally along the length of the foot member, a base, a first shaft, a second shaft, a third shaft, a fourth shaft, a pair of braces, a cam, the cam having an off-center first aperture or in the alternative, a cam having geometry and aperture combination that allows movement in one direction and that binds in the other direction of movement, at least one second aperture, and a recess, the recess shaped and adapted to receive a link, the first aperture shaped and adapted for receiving a first shaft therethrough and wherein the first shaft can revolve therein, a housing, the housing having at least two threaded apertures shaped and adapted to receive a bolt, the link connected to the housing using a fourth shaft positioned through a first link aperture in the link and a least one aperture located in a flange abutting from the housing and having at least one second link aperture at the end of the link opposing the housing, at least two bolts, at least two compression springs, an adaptor, the adaptor having at least two bolt apertures shaped and adapted for receiving a bolt therethrough, at least two set screws, wherein the arm has a first apertures located at the first end and a second aperture located at the second end, the apertures sized and spaced to receive a second shaft therethrough and wherein the second shaft can revolve therein, wherein the base has at least one aperture, the aperture sized and spaced to receive the second shaft therethrough, wherein the bearings are in lateral opposition fixedly attached to the foot member, the first end of the arms positioned between the two bearings and in contact with the soft bumpers, the soft bumpers secured to the foot member and supporting the arms, the base centered between the two bearings and in contact with the stiff bumpers, wherein the braces are positioned and secured between the second end of the arms, wherein the cam is centered between the second end of each arm and having a surface in intermittent contact with a surface of the base, the surface contact dependent upon the rotated position of the cam, wherein the link aperture is positioned in-line with the second aperture of the cam and a third shaft positioned therethough and wherein the third shaft can revolve therein, wherein the adaptor is positioned to the housing, wherein each bolt is positioned through an aperture in the adaptor and is threaded into a threaded aperture in the housing, wherein each compression spring is placed longitudinally encircling the bolt thread between the bolt head and the adaptor, and the bolt is reversibly threaded through the housing bolt aperture and into a threaded recess in the second end of the arm. In an alternative embodiment the invention provides the prosthetic foot as disclosed herein, further comprising a pair of spacers, the spacer shaped and adapted for placement between a bearing and an arm.

In a yet other alternative embodiment the invention provides a prosthetic foot, the prosthetic foot comprising a heel, a foot member, a shin member, an ankle joint, the ankle joint having a plurality of equilibrium points and wherein a user of the prosthetic foot can proceed over a surface without overbalancing. In a preferred embodiment the ankle joint further comprises a locking mechanism. In a more preferred embodiment the locking mechanism is selected from the group consisting of, a pair of cams, a ratchet mechanism, a ball joint, a wrap spring clutch, and the like.

In one embodiment the prosthetic foot comprises a composition selected from the group consisting of stainless steel, copper, aluminum, titanium, metal matrix composite, metal alloy, such as NITINOL, DELRIN (acetal), acrylonitrile butadiene styrene (ABS), nylon, polypropylene, polybromate, polycarbonate, glycolised polyethylene terephthalate (PETg) copolyester, olytetrafluorethylene (PTFE), ePTFE, polypropylene, a polymer, glass fiber-resin composites, carbon fiber resin composites, and the like.

The invention also provides a method for providing normal gait in an amputee, the amputee having lost a lower limb extremity, the method comprising (i) providing the prosthetic foot disclosed herein; (ii) attaching the prosthetic foot to the lower limb of the amputee; (iii) allowing the amputee to ambulate, the method resulting in providing normal gait to the amputee.

In one embodiment the invention provides devices that can automatically adapt to different surface inclinations and to shoes of different heel heights. These devices also take on biomimetic ankle-foot roll-over shapes by utilizing biomimetic foot shape and ankle stiffness (for example, shapes and stiffness properties that mimic the biologic system). Lastly, the devices more closely mimic the able-bodied ankle-foot mechanism in the period from opposite heel contact to toe off because they can achieve plantarflexion beyond neutral during this unloading phase of gait. The devices then bring the ankle back into a neutral or slightly dorsiflexed position just after toe off to provide toe clearance for the swing phase. The plantarflexion beyond neutral at late stance may reduce the amount of energy needed for walking for individuals using the devices by increasing the return of stored energy to the leg. This may in turn help prosthesis and orthosis users to walk at consistently faster speeds.

The ankle-foot devices automatically adapt to various walking surfaces using stiffness-based control and few sensing devices. This mode of control may be preferable to damping-based control (Koniuk, 2002) because it allows for return of stored energy. In theory, equilibrium-point prosthetic ankle-foot devices of the invention are designed to store and return energy with a high degree of efficiency.

BRIEF DESCRIPTION OF THE SEVERAL VIEWS OF THE DRAWINGS

FIG. 1 illustrates an exemplary embodiment of the invention.

FIGS. 2A and 2B illustrate a linear braking mechanism exemplifying the invention.

FIGS. 3A through 3K illustrate an exemplary loading phase of a device of the invention.

FIG. 4 illustrates an exemplary torsion curve of a pair of neutralizing springs (NS; prior art) showing $\zeta$, the point of intersection of the cave at T=0 (the equilibrium point).

FIG. 5 illustrates an exemplary torsion curve of a "triceps surae" spring (TS; part of the instant invention) showing $\beta$, the point of intersection of the curve at T=0 (the equilibrium point).

FIG. 6 illustrates an exemplary torsion curve of the invention showing that the torsion curve has at least two equilibrium points. FIGS. 6A and 6B exemplify the invention in use up a gradient (slope). FIGS. 6C and 6D exemplify the invention in use on a level surface. FIGS. 6E and 6F exemplify the invention in use down a gradient (slope). FIGS. 6B, 6D, and 6F illustrate the predicted curve of the invention in use showing the transition point (intersection of the NS curve with the TS curve).

FIGS. 9A and 9B illustrate an exemplary device of the invention.

FIGS. 10A and 10B illustrate illustrates an exemplary device of the invention in use.

FIG. 11 illustrates two stages during operation of the prosthetic ankle-foot system showing, in part, the relative positions of the internal gear and external gear in use. FIG. 11A shows the device in a loaded state. FIG. 11B shows the device in an unloaded state.

FIGS. 12A and 12B illustrate an exploded illustration of an exemplary device of the invention as well as an exemplary illustration of the device in use.

FIG. 13 illustrates two stages during operation of the prosthetic ankle-foot system showing, in part, the relative positions of the base and the cam during active motion of the use. FIG. 13A shows the device in a loaded state. FIG. 13B shows the device in an unloaded state.

FIG. 14 through 20 illustrate a sequence of images of the invention showing how the invention works on inclines.

FIGS. 21 through 31 illustrates a sequence of images of the invention showing how the invention works and discloses plots of ankle dorsiflexion/plantarflexion against time.

DETAILED DESCRIPTION OF THE INVENTION

Figures 3C, 3D, 3E:
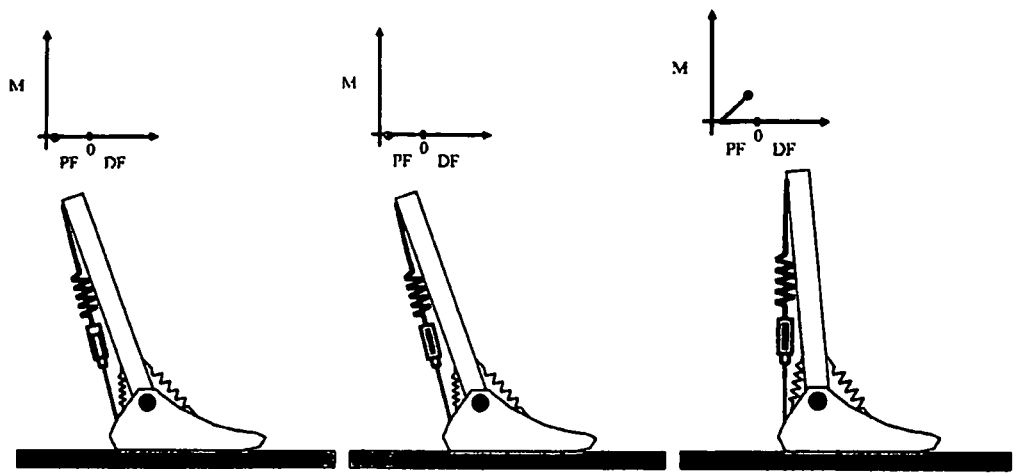

The equilibrium point prosthetic and orthotic ankle-foot devices work by utilizing a natural movement of the ankle during early stance phase to adjust the resting length, also known as the equilibrium point, of a spring mechanism. The devices are named after Feldman's equilibrium point hypothesis ((1986) "Once more on the equilibrium-point hypothesis (lambda model) for motor control" J. Motor Behav. 18: 17-54) regarding the control of human movements. As used herein, the term "equilibrium point" is the angular position of the ankle system when the net external torques (not including those applied by components within the system or in the absence of external forces and moments) are equal to zero.

The premise of the design is the use of two sets of elastic elements, such as a spring or the like, wherein one set dominates the response of the system when an engaging/disengaging mechanism, such as brake or the like, is engaged and another set that dominates the response when the engaging/disengaging mechanism is released. Allowing the foot to "find" the walking surface during early stance and then applying the engaging/disengaging mechanism will allow the device to inherently and automatically adapt to a variety of terrain and/or shoe heel heights. Refer to FIGS. 1-8, 13-30, and 32 for drawings illustrating the embodiment of the invention.

The device comprises two sets of springs: A set of "neutralizing springs" (NS) and a larger and stiffer "triceps surae" spring (TS spring) that is in series with a braking or locking component. The "neutralizing" springs are configured such that their equilibrium point (point of zero ankle moment) is at a point where the ankle is neutral or slightly dorsiflexed (see FIG. 4, at $\zeta$, below). The "triceps surae" spring may be located where the corresponding muscle group (gastrocnemius and soleus muscles) would be (that is, in or proximal to the calf region). This larger and considerably stiffer spring is in series with an engagement means (for example, a braking or locking component) as stated earlier. Preferably, the TS spring and the engagement/disengagement (braking or locking) mechanism, are in series. In the alternative, the TS spring/engagement combination and the NS spring(s) are in parallel. In one embodiment, the engagement mechanism may be considered to be a variable damper that switches between near-zero damping to extremely high damping values.

At all times, the neutralizing springs (ns) are acting according to the following equation ($k_{ns}$, impedance factor; could be a function of $\theta$, the ankle dorsiflexion angle). This is also an example of the prior art (FIG. 4):

$$T_{ns} = k_{ns}(\theta - \zeta),$$

where
$T_{ns}$=torque due to neutralizing springs
$\theta$=ankle dorsiflexion
$\zeta$=ankle dorsiflexion bias Between the "trigger (engagement) time" to toe-off (the beginning of swing phase), the triceps surae spring (ts) is also engaged according to the following equation ($k_{ts}$, impedance factor, could be a function of $\theta$, the ankle dorsiflexion angle). This is also an example used to illustrate the instant invention (FIG. 5):

$$T_{ts} = k_{ts}(\theta - \beta),$$

where
$T_{ts}$=torque due to triceps surae spring
$\theta$=ankle dorsiflexion
$\beta$=ankle angle at the trigger time The ankle angle at the trigger time ($\beta$) changes for different terrain: $\beta$ increases for uphill terrain causing the curve to shift to the right; $\beta$ decreases for downhill terrain, causing the curve to shift to the left.

For the preferred embodiment, the trigger time is the time of foot flat (in early stance phase). It is conceivable that other trigger times could be used, though, including a time at which the pylon reaches a particular orientation in stance phase (for example, near vertical). So the overall torque at the ankle (T) can be described as follows:

$$T = \begin{cases} T_{ns}; & t_{toe-off} < t < t_{trigger} \\ T_{ns} + T_{ts}; & t_{trigger} < t < t_{toe-off} \end{cases}$$

Note that the act of walking is cyclic so the toe-off and trigger times occur in continuous and alternating order. In addition to this, the invention provides not only automatic adaptation in the sagittal plane, but also envisions devices that can adapt to three-dimensional changes in terrain, for example, side slopes, and combinations of side and upward sloping surfaces.

At the transition point, the system engages and sets the equilibrium point of at least one torsional element. This transition switches the system between a low impedance state to a high impedance state. Because the transition point can be tied to a gait event, such as foot flat, the equilibrium point of at least one torsional means can be adjusted in the device, leading to a change in the system's equilibrium point. This adaptability allows for automatic adjustment to different walking surface inclinations.

As shown in FIGS. 6A through 6F, at initial contact of the heel with the walking surface, the brake is unlocked allowing free movement. The neutralizing springs are compressed (and/or stretched) as the ankle moves into a plantarflexed position (that is, as the forefoot comes down to make contact with the floor). During this time, the triceps surae spring remains at its resting length while the braking mechanism changes its length or angle (depending on linear or rotational realization of the device). At the time when the ankle stops moving in the direction of plantarflexion and begins to move into dorsiflexion (that is, at the point of maximum plantarflexion), the braking mechanism locks. This locking action sets the equilibrium point of the triceps surae spring at the point of maximum plantarflexion. As the person rolls forward (during Perry's second rocker (1992) Gait Analysis: Normal and Pathological Function, Thorofare, SLACK Inc.), the triceps surae spring is stretched creating an appropriate ankle moment for walking or the like. After opposite heel contact, the load is removed from the device and the triceps surae spring returns stored energy to the leg by plantarflexing. When the load is almost fully removed, the ankle will be close to the resting length of the triceps surae spring and the ankle will be at an angle of plantarflexion that is close to that at which the braking mechanism was locked. When the ankle plantarflexion angle comes within a threshold value of the amount that it acquired in early stance, the braking mechanism is released. As the foot leaves the floor in early swing, the neutralizing springs bring the ankle into a neutral or slightly dorsiflexed position (back to position at $\zeta$) to allow for better clearance between the toe and the floor in swing phase. In the alternative, the braking mechanism can be released when a load, such as the weight of the user, is released from being applied to the device.

The control of the braking mechanism could be accomplished using instrumentation that takes input from a potentiometer or rotational encoder. Other possible methods of setting the braking mechanism include utilization of a pressure sensor under the forefoot and/or the use of cams or weight-activated locks (see Examples section below).

Improvements of the Invention Over Existing Technologies

The improvements over existing technologies include the ability to adapt to various shoe heel heights and walking inclinations and the provision for plantarflexion at late stance. The device may prove to be superior in energy storing and release characteristics over existing devices although this remains to be seen. Koniuk (2002) has stated the claim of adaptation to shoe heel height and walking inclination in a recently patented design that utilizes damping-control. Our design differs from Koniuk's (2002) in that it utilizes stiffness control and biomimetic foot roll-over shape, allowing the device to achieve an ankle-foot roll-over shape similar to that of an able-bodied person's ankle-foot system during walking, while also allowing for energy return and plantarflexion in late stance.

Design and Manufacture of the Invention

This design is realized in a number of ways. Rotational springs, linear springs, or combinations of the two are used to supply the appropriate impedances about the ankle at different stages of the walking cycle. In the following diagrams, however, the concept of the device will be illustrated using linear springs to describe an "equilibrium-point" prosthetic ankle joint.

FIG. 1 is an exemplary diagram of the device pointing out the various components of the device. FIG. 2 shows how the linear braking mechanism (that is, linear lock/unlock) is represented in FIG. 3. FIG. 3 shows the action of the ankle-foot device throughout the gait cycle.

FIG. 4, as disclosed above, illustrates a torque curve plot of the prior art using two neutralizing springs (NS). Note that the single equilibrium point at $\zeta$. There is no transition point since there is only one plane of movement.

FIG. 5, as disclosed above, illustrates a torque curve plot using a single "triceps surae" spring (TS). Note the single equilibrium point at $\beta$.

FIG. 6 illustrates exemplary torque curve plots of the invention showing that there are two equilibrium points. In FIG. 6, the dotted line represents the predicted torque curve of an NS spring. The dashed line represents the predicted torque curve of a TS spring. The thin solid line represents predicted torque curve of the combination of the NS and the TS. The thick solid line represents an actual torque curve plot showing the transition point ($P_t$). FIGS. 6A and 6B show the invention in use on an incline, FIGS. 6C and 6D show the invention on a level surface. FIGS. 6E and 6F show the invention in use on a decline. FIGS. 6B, 6D, and 6F additionally show the path (heavy line) of a single gait; note the transition point (intersection) of the two torque curves. FIGS. 6B, 6E, and 6F show that the invention can have multiple transition points and that relative position of the transition point on the curve plot is related to the gradient (incline, level, or decline) of the surface. Note also that the torque curve shifts to the left (negative ankle dorsiflexion angle) from going uphill (incline), through level surface, and going downhill (decline).

Figure 7:
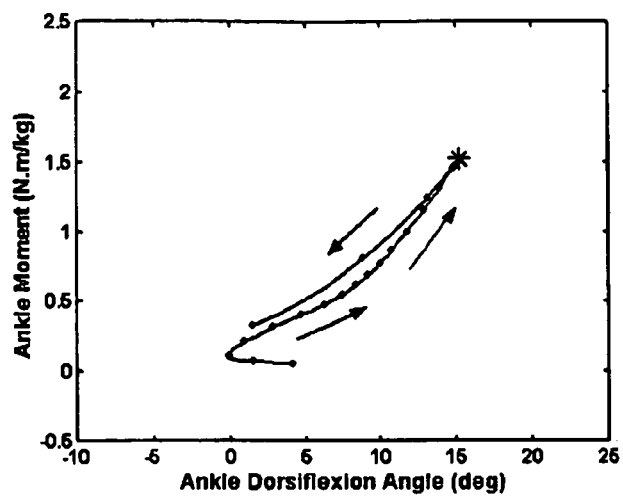
FIG. 7 illustrates average ankle moment plotted against dorsiflexion angle of twenty-four able-bodied subjects.

The springs are chosen to replicate impedance values found for able-bodied human walking (Hansen et al., (2004b) "The Human Ankle During Walking: Implications for Design of Biomimetic Ankle Prostheses and Orthoses" J. Biomech. 37: 1467-1474). These values change somewhat with walking speed but will be designed based on slow to normal walking speeds. The characteristics for extremely fast walking speeds cannot be mimicked using a passive system (Hansen et al., 2004b, supra). A diagram of the ankle impedance characteristics found for 24 able-bodied ambulators is shown in FIG. 7. Notice how this characteristic matches closely the characteristic drawn in the diagrams of FIGS. 3-6 showing that the prosthetic system and the ankle-foot device of the invention automatically adapt to different surface conditions.

Figures 8A, 8B:
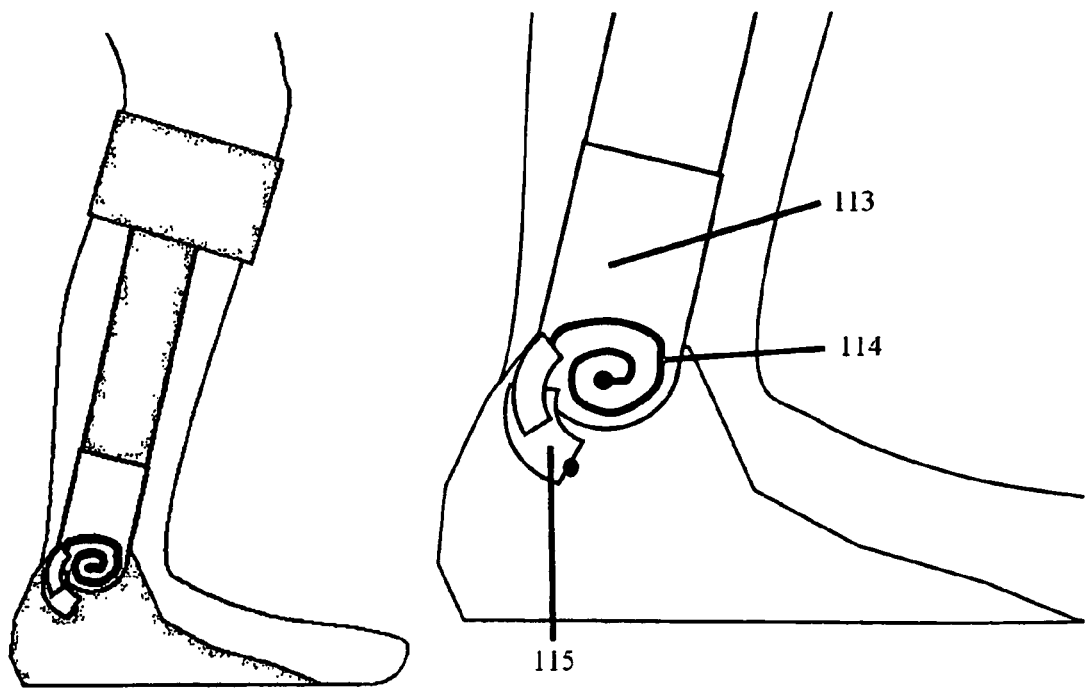
FIGS. 8A and 8B illustrate an equilibrium-point ankle-foot orthosis (AFO).

This concept can also be used in a rotational sense and in the field of orthoses. An equilibrium-point ankle-foot orthosis (AFO) design that uses rotational components is shown in FIG. 8.

Exemplary Embodiments of the Invention

Our laboratory has developed prosthetic ankle joint devices having at least two equilibrium points. In another alternative, the device has at least three equilibrium points. The first exemplary device (device #1) is shown in FIG. 9. This device uses a semicircular knurled disc that interacts with a circular knurled cam. When the circular cam is engaged and the ankle starts to dorsiflex, the semicircular disc compresses a bumper. This bumper acts as the triceps surae spring for this design. The neutralizing springs are realized as elastomeric cords crossing the ankle joint. Results of the first device in use on a treadmill suggested that is was adapting to different terrain(s).

A second exemplary device (device #2) that makes use of a weight-activated locking mechanism is shown in FIGS. 10-11. This device allows plantarflexion in early stance and locks when the upper plate (with internal gear, 32, attached thereto) comes into contact with the semicircular external gear (33). After the internal gear and external gear are engaged (FIG. 11B), dorsiflexion of the ankle causes deformation of a bumper (6; which acts as the triceps surae spring for this design). Neutralizing springs are realized in this design by two softer bumpers (10; see FIG. 10 description below for more explanation of this device).

There are advantages and disadvantages of designs #1 and #2. The advantages of the first design include the fact that it should always allow the full range of early stance plantarflexion before the cam "locks in" the use of the triceps surae bumper. The second design will lock at a specified load and has the potential to lock (and/or unlock) too early or too late. Additionally, the first design can be altered to allow locking of the cam at a later time in the stance phase, for example when the pylon becomes vertical. However, making this adjustment would remove the feature of late stance plantarflexion with the device. The advantages of the second device are that it could more likely be created with a purely mechanical system and would not need sensors or active mechanisms to operate. The first device needs an active component to disengage the cam (locking mechanism) after toe off. Currently the cam is removed by having the user pull a Bowden cable.

A third device (device #3) was developed using the strengths from devices #1 and #2 (see FIGS. 12 and 13). The third device utilizes a weight-activated cam-locking mechanism to engage the TS spring (an anterior bumper) (see FIGS. 13A and 13B). The ankle can still "roll-back" into plantarflexion if necessary after the cams have been engaged, and the cams are disengaged by the weight-activation system when load is removed.

In one embodiment the ratio of the radius of the cam to the radius of the base is selected from the group consisting of 2:1, 3:1, 4:1, 5:1, 6:1, 7:1, 8:1, 9:1, 10:1, and intermediate values thereof. In a preferred embodiment, the radius of the base and the radius of the cam have a ratio of about 4:1.

The expected commercial applications include ankle-foot prostheses and orthoses for persons with disabilities. These components would hopefully improve the mobility of these persons by allowing them to automatically adapt to various walking surfaces while at the same time giving them biomimetic ankle-foot roll-over shape as well as storage and release of energy from the prosthesis at the appropriate times. The device can also allow for automatic adaptation for different heel heights, allowing a user to use a variety of different shoes. The devices can also be used in walking machines, legged robots, and toys.

The prosthetic foot can be manufactured from a variety of compositions and a variety of combination of compositions. The prosthetic foot can comprise a composition selected from the group consisting of stainless steel, copper, aluminum, titanium, metal matrix composite, metal alloy, such as NITINOL, DELRIN (acetal), acrylonitrile butadiene styrene (ABS), nylon, polypropylene, polybromate, polycarbonate, glycolised polyethylene terephthalate (PETg) copolyester, olytetrafluorethylene (PTFE), ePTFE, polypropylene, or another polymer, glass fiber-resin composites, other composite materials, and the like, and, optionally, that can be easily machined, compression molded, or injection molded to the required shape.

The prosthetic foot can be shaped and sized for purposes of mass manufacture in a standard size and shape. In the alternative, it can be manufactured to specifications for a single individual. The prosthetic foot can be manufactured using modular components, the modular components having different shapes, sizes, and compositions.

The ankle of the prosthetic foot can comprise a locking mechanism, for example the locking mechanism can beselected from the group consisting of, a pair of cams, a ratchet mechanism, a ball joint (such as disclosed in U.S. Pat. No. 6,217,249 to Merlo, issued Apr. 17, 2001), selectively engageable and disengagable mechanisms, and joint locking mechanisms as disclosed in, for example, U.S. Pat. No. 6,159,248 to Gramnas, issued Dec. 12, 2000, U.S. Pat. No. 6,436,149 to Rincoe, issued Aug. 20, 2002). The prosthetic system can also be combined with at least one microprocessor comprising a software program or other instructional means that in combination can provide a control means. The control means can measure the torsion within the system and thereby control the engagement means and the torsional means during each step cycle or gait cycle. Such microproccessors and software programs are well known to those of skill in the art.

There now follows a non-exhaustive list of different devices and/or mechanisms known to those of skill in the art that can be used with the invention.

Engagement Means

Types of Clutch

Automatic clutch, backstopping clutch, ball clutch, bidirectional clutch, brake-clutch combination, cam clutch, cam and roller clutch, centrifugal clutch, cone clutch, detent slip clutch, disc clutch, dog clutch, double clutch, double-spring clutch, dual-spring slip clutch, duplex clutch, driving clutch, eddy current clutch, electrostatic clutch, expanding shoe clutch, externally controlled positive clutch, external control clutch, internal control clutch, fixed-field clutch, fluid clutch, free-wheeling clutch, friction clutch, multiple disc clutch, détente clutch, plate clutch, hysteresis clutch, indexing clutch, internally controlled clutch, jaw clutch, lawnmower clutch, bidirectional locking clutch, locking clutch, magnetic friction clutch, magnetic particle clutch, magnetic fluid clutch, magnetostrictive clutch, mechanical clutch, mercury-gland clutch, multidisk clutch, multistation clutch, one-way clutch, overload relief clutch, overriding clutch, overrunning clutch, planetary transmission clutch, plate clutch, roller clutch, roller clutch, rotating-field clutch, sliding-key clutch, slip clutch, spiral-band clutch, sprag clutch, spring clutch, spring and ball radial detent clutch, station clutch, tooth clutch, torque limiting clutch, trip clutch, wedging ball or roller clutch, and wrap spring clutch.

Types of Brake

Air brakes, anti-lock brakes, coaster brakes, disc brakes, drum brakes, eddy current brakes, electric brakes, friction brakes, hub brakes, hydraulic brakes, multi-disc brakes, power brakes, rim brakes, spoon brakes, band brakes, and caliper brakes.

Types of Lock

Cruciform lock, cylinder lock, deadbolt lock, disc tumbler lock, electronic lock, magnetic lock, electric strike lock, level tumbler lock, Chubb detector lock, protector lock, padlock, pin tumbler lock, wafer tumbler lock, warded lock, 5 lever lock, keycard lock, rim lock, combination lock, and pin lock.

Torsional Means

Types of Spring

Coil or helical spring, tension spring, compression spring, leaf spring, v-spring, spiral spring, clock spring, cantilever spring, Belleville washer spring, spring washer, torsion spring, gas spring, rubber band, elastic elements, bumpers, umbrella springs, conical springs, taper springs, disc spring, and extension spring.

Types of Damper

Backdraft damper, barometric damper, butterfly damper, curtain damper, dual tube damper, flap damper, free-piston monotube damper, guillotine damper, louvre damper, sliding damper, and vibration damper.

REFERENCE NUMERALS

1. Foot member
2. Bearing
3. Arm
4. First cam

5. Spacer
6. Spring or second bumper (Torsion means)
7. Block
8. Set screw
9. Second cam (Engagement means)
10. Spring or first bumper (Torsion means)
11. First shaft
12. Second shaft
13. Third shaft
14. Fourth shaft
15. First aperture
16. Second aperture
17. Recess
18. Link
19. Housing
20. Threaded aperture
21. Bolt
22. First link aperture
23. Compression spring
24. Adaptor
25. Bolt aperture
26. First aperture (arm)
27. Second aperture (arm)
28. Aperture (first cam)
29. Surface (adaptor)
30. Surface (housing)
31. Bolt aperture (arm)
32. Internal gear
33. External gear
101. Ankle-foot system
102. "Triceps surae" (TS) spring means
103. Linear Lock/Unlock means
104. "Neutralizing" spring(s) means
105. Ankle Joint The invention will be more readily understood by reference to the following examples, which are included merely for purposes of illustration of certain aspects and embodiments of the present invention and not as limitations.

EXAMPLES

Example I

Use of Weight-Activation to Control the Ankle Mechanism

Engagement can be set to occur upon loading of the device by the user's weight. In this case, a mechanism is in place that engages the triceps surae torsional means after a sufficient amount of body weight has been applied to the system. Upon unloading of the device, the engagement reverses (that is the triceps surae spring is disengaged from the rest of the system). Examples of this type of engagement are shown in devices #2 and #3.

Example II

Use of Potentiometers or Encoders to Control Locking-Unlocking Mechanisms

Figure 33:
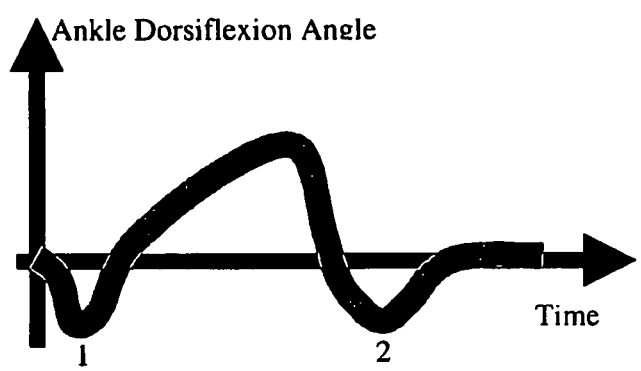
FIG. 33 illustrates a theoretical plot of ankle dorsiflexion/plantarflexion against time for the system or device showing the time at when a first minimum dorsiflexion angle is reached (1) where the brake, lock, or clutch engages and would remain engaged until a second minimum dorsiflexion angle is reached (2).

The projected ankle motion of this device is shown in FIG. 33. The potentiometers or encoders measure these angles during use of the device. In early stance, the locking mechanism may be unlocked. When the rotational sensor indicated that a minimum dorsiflexion angle is reached (at time 1), the system will signal to engage the locking mechanism. This mechanism remains engaged until this angle is approached at the end of stance phase (at time 2), at which time the system unlocks and allows the neutralizing springs to bring the ankle back to neutral for swing phase.

Example III

Use of Forefoot Pressure Sensors to Control Locking-Unlocking Mechanisms

An alternative way to control the locking and unlocking mechanism is to use a forefoot pressure sensor. In early stance, the ankle plantarflexes until the forefoot contacts the walking surface. At this first contact with the forefoot pressure sensor, the locking mechanism may be engaged. Forefoot contact remains until the toe comes off of the ground at the end of stance. At this time, the pressure goes to zero and the locking mechanism could be unlocked, allowing the neutralizing springs to bring the ankle back to neutral for swing phase.

Example IV

Use of Pylon Moments to Control Unlocking of a Cam Mechanism

Devices to measure moments on the pylon maybe used to indicate the time at which a cam locking mechanism should be unlocked. The cam mechanism described by device #1 automatically sets the equilibrium point of the ankle in early stance but needs a control signal at late stance to release the cam. After the middle cam is engaged and the front bumper is compressed, a moment is produced on the pylon that can be measured. After the load is removed from the leg, this moment should go to zero. Thus a circuit or microprocessor could note the falling edge of a pylon moment and use this falling edge as a trigger to unlock the cam mechanism after toe off.

FIG. 1. Diagram of the "Equilibrium-Point" Prosthetic Ankle Joint.

FIG. 2. The linear braking mechanism (that is, "linear lock/unlock") is shown in the following figures to be clear when it is unlocked and is shown in gray when it is locked.

FIGS. 3A, 3B, and 3C. The initial loading phase for the device. The braking mechanism is unlocked allowing the foot to be lowered to the floor against the resistance of the neutralizing springs. This action mimics what Perry (1992, supra) refers to as the first rocker or the heel rocker and corresponds to the first double-support part of the gait cycle.

Figures 3F, 3G, 3H:
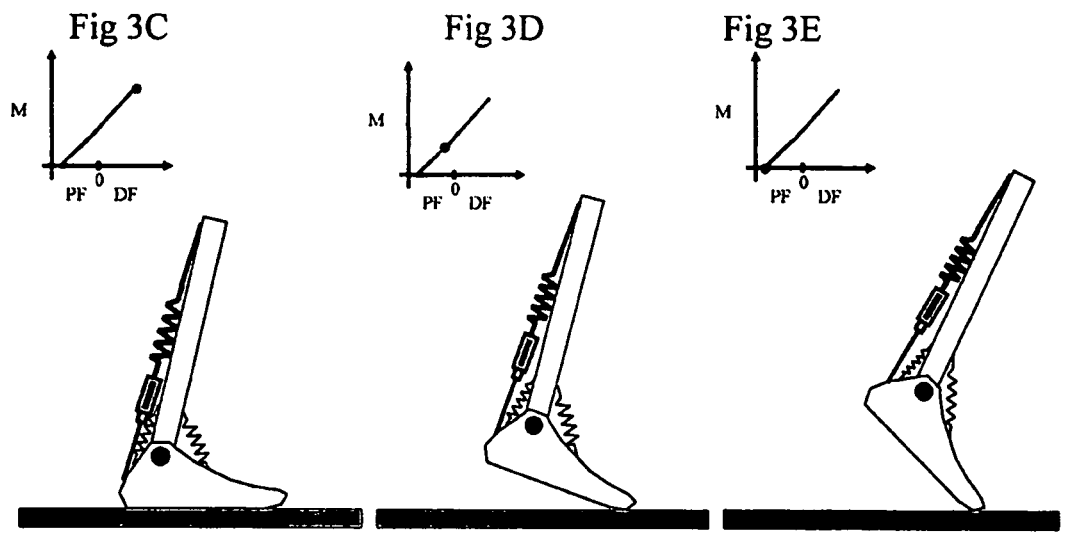

FIGS. 3D, 3E, and 3F. Continuing from FIG. 3C, when the ankle dorsiflexion angle stops decreasing and begins to increase the braking mechanism locks (left). The person then rolls over on the ankle joint as the triceps surae spring is stretched (middle and right). Perry (1992, supra) refers to this as the second rocker or ankle rocker. This period of time corresponds most closely with the single-limb stance period of gait.

Figures 3I, 3J, 3K:
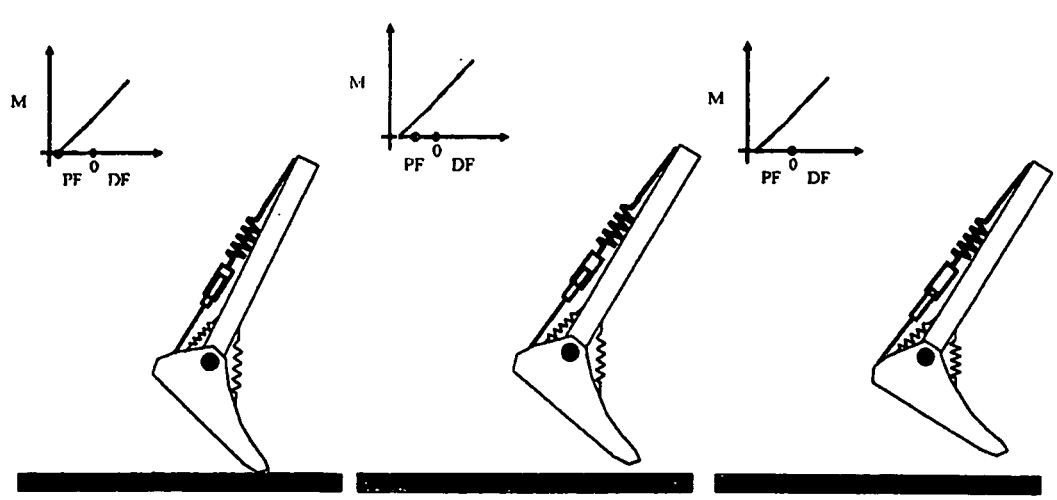

FIGS. 3G, 3H, and 3I. Continuing from FIG. 3F, after the opposite heel contacts (which would be FIG. 3J) the load is rapidly removed from the system and some of the stored energy can be released back to the leg. The series of FIGS. 3G through 3I show this unloading period. At the end of the unloading period, when the dorsiflexion gets near the point where the braking mechanism locked, the brake is released. Perry (1992, supra) refers to this period as the third rocker or the forefoot rocker. This period of time corresponds most closely with the second part of double-limb support of walking.

FIGS. 3J and 3K. Continuing from FIG. 3I, as the braking mechanism is unlocked the foot is coming off the ground and preparing to swing. In order to avoid stubbing the toes, the ankle needs to go back into a neutral or slightly dorsiflexed position. Since the braking mechanism is unlocked, the neutralizing springs again dominate and pull the foot upwards to a proper position for swing phase.

FIG. 7. Average ankle moment versus dorsiflexion angle plot for 24 able-bodied ambulators (adapted from Hansen et al., 2004b). Springs will be selected such that the overall impedance of the ankle-foot device mimics this characteristic. The asterisk shows the time at which opposite heel contact occurs. Theoretical ankle moment versus ankle dorsiflexion characteristics for the ankle joint are shown in FIG. 3-6.

FIG. 8. Equilibrium-point ankle-foot orthosis (AFO). This design is similar to the equilibrium-point prosthetic ankle-foot mechanism except it uses rotational components instead of translational. The neutralizing springs are not shown but are provided by technology that is already available (Klenzak ankle units). These joints can be altered to allow different amounts of dorsiflexion or plantarflexion. They contain spring elements that could act as the neutralizing springs. Other neutralizing joints could also be used. The main elements shown here are the rotational "triceps-surae" spring in series with a rotational lock-unlock mechanism.

FIG. 9. Equilibrium-point prosthetic ankle joint device that incorporated a cam locking mechanism. (FIG. 9A) Drawing of the ankle device. (FIG. 9B) Drawing of the device with one side-piece removed so that the cam mechanism can be seen. The joint utilized a large knurled semicircular section that compressed a rubber bumper when the cam was engaged. In early stance, the cam allowed plantarflexion until foot flat. Following foot flat, the cam engaged the semicircular section that compressed the anterior bumper. In this design, the bumper represents the triceps surae spring. The drawings do not have neutralizing springs. Two pillow block bearings (2), (one is shown and one is hidden) are connected to a footplate (1). Between the pillow block bearings, two upper arms (3) and a middle cam (4) are sandwiched. A shaft (not shown) was used through hole (a) to connect the pillow blocks (2), upper arms (3), and middle cam (4). At the top of the upper arms, a spacer piece (5) was used to keep the upper arms parallel. A hole (c) may be drilled and tapped in the center of this spacer piece to allow connection with the rest of the prosthesis. The middle cam had its hole drilled at the center of the outer radius. The middle cam was cut away in the front to allow interaction with a spring or rubber bumper (6). This spring or rubber bumper is kept from displacing forward by a containment block (7). A set screw (8) that interacted with the back of the middle cam was used to preload the spring or rubber bumper (6). A smaller cam (9) with offset hole was pinned to the upper arms (3) through hole (b). This smaller cam allowed backward rotation of the upper arms with respect to the middle cam, but when engaged the smaller cam bound with the middle cam preventing forward rotation. Therefore in early stance, the smaller cam allowed plantar flexion of the ankle with no effects on the middle cam. After maximum plantar flexion in early stance phase, as dorsiflexion began, the small cam bound against the middle cam, rotating the upper arms forward about hole (a), compressing the spring or rubber bumper. The rubber bumper represented the "triceps surae" spring of the conceptual design. The neutralizing springs are not shown in these drawings. In device #1, the neutralizing springs were elastic cords. The neutralizing springs could easily be incorporated as softer springs or bumpers that interact directly between the upper arms and the footplate, as is shown in device #2 (FIGS. 10 and 11).

With this device, a locking cam was used to engage the triceps surae spring. This device required an active component at the end of stance to disengage the cam. In the first device, the cams were disengaged using a pull cord through a flexible tube. This cord went superior to the smaller cam (from the back) and attached to its anterior side. The cord was pulled posteriorly after toe off to disengage the smaller cam from the middle cam, allowing the neutralizing springs to return the ankle to its neutral position for swing phase. In future versions, this unlocking mechanism can be a small electric motor that winds up a cord or a linear actuator working through levers to disengage the smaller cam from the middle cam.

FIG. 12. Exploded illustration of device #3 with labels for each component. Note that the Set Screws (8) are inserted into the corners of the Upper Housing (19) and cannot be seen in this view. The two pillow block Bearings (2) attach to the Foot Plate (1) and house the Shaft (11), which serves as the axis of rotation for the ankle. The two Arms (3) also rotate about the Shaft (11) and are held vertical by the two Soft Bumpers (10) and are held parallel to each other by the two Braces or Spacers (5). In between the Arms (3) is the Base (or first cam; 4) that is held vertical by the Stiff Bumper (5, that also rotates about the Shaft (11). The Arms (3) hold a pin (or shaft; 13 that serves as the axis of rotation for the Cam (9). This axis is slightly offset from the center of the Cam (9), allowing backward rotation of the Arms (3) with respect to the Base (4), but when engaged the Cam (9) jams into the Base (4), preventing forward rotation.

The Arms (3) also hold the four Shoulder Bolts (21) in place. The Adaptor (24; which connects to the user's prosthetic pylon) is attached to the Upper Housing (19); these two pieces can slide up and down the Shoulder Bolts (21) and have the four Compression Springs (23) under them to resist contact between the Upper Housing (19) and the Arms (3). Four Set Screws (8) protrude from the bottom face of the Upper Housing (19) and their length determines the maximum distance that the Upper Housing (19) can travel towards the Arms (the Upper Housing "bottoms-out" when the Set Screws (8) hit the Arms (3)). The Upper Housing (19) holds a pin (or shaft; 14) that pins the proximal end of the Link (18). The distal end of the Link (18) is pinned (shaft 13) to the Cam (9), so that as the Upper Housing (19) moves downwards, the Link (18) forces the Cam (9) to rotate onto the Base (4).

The overall mechanism utilizes the user's body weight to change the stiffness of the ankle joint. As the user steps onto the mechanism, the rotation of the Arms (3) is only resisted by the Soft Bumpers (10; the mechanism is in the "unlocked" or "low-stiffness" mode) and the Foot Plate (1) is easily able to reach foot flat. The user's weight shifts onto the mechanism and the Upper Housing (19) presses down onto the Compression Springs (23). As the Upper Housing (19) slides down the Shoulder Bolts (21) it pushes the Link (18) into the Cam (9), causing the Cam (9) to rotate down and jam into the Base (4) (see FIG. 13A).

At this point, as the Arms (3) try to rotate forward (ankle dorsiflexion) the Base (4) is resisted by the anterior Stiff Bumper (6; the mechanism is now in the "locked" or "high-stiffness" mode). Towards the end of stance the user's weight comes off of the mechanism and the Compression Springs (23) push the Upper Housing (19) away from the Arms (3). This pulls superiorly on the Link (18), rotating the Cam (9) off of the Base (4) (see FIG. 13B).

The rotation of the Arms (3) is once again only resisted by the Soft Bumpers (10), which force the Arms (3) back into a neutral alignment (the mechanism is back in the "unlocked" or "low-stiffness" mode) to prepare the mechanism for the next step.

FIGS. 14 through 20 illustrate different exemplary stages of the invention when being used to walk upon inclined surfaces.

FIGS. 21 through 31 illustrate different exemplary stages of walking having controlled plantarflexion using neutralizing springs as embodied in the invention.

Figure 32:
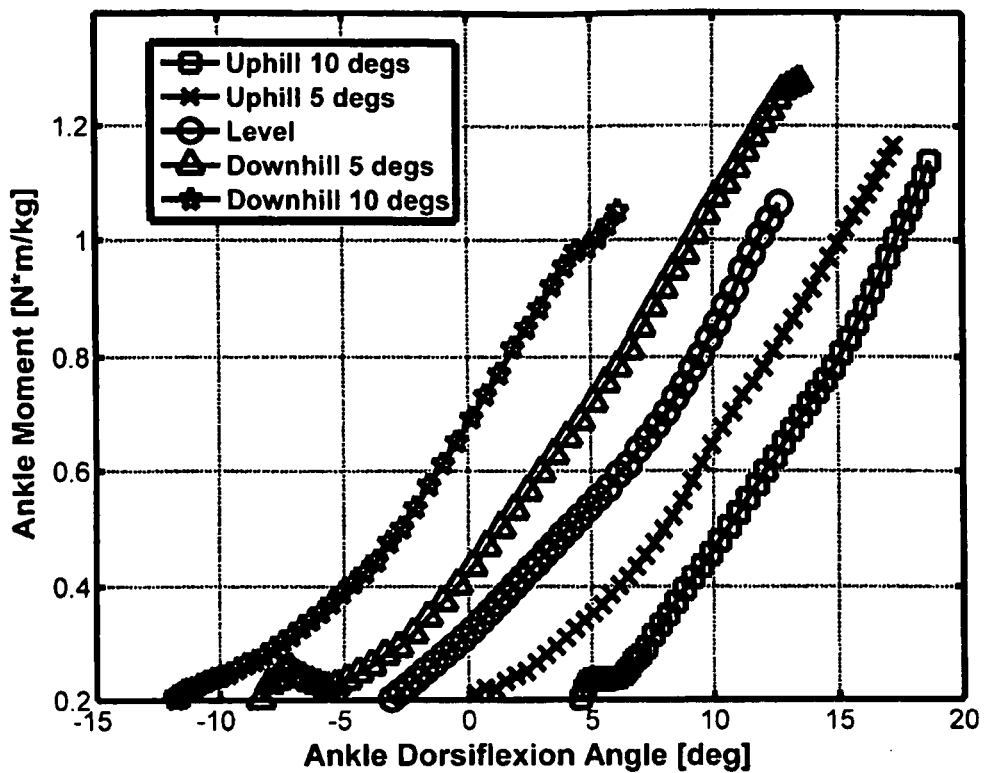
FIG. 32 illustrates a series of experimental data obtained during testing of a device of the invention on inclined, level, and declined surfaces.

FIG. 32 illustrates experimental data from one subject having unilateral transtibial amputation who was using device #3. FIG. 32 shows that the torque curve of the invention used in a single gait on a variety of inclined, level, and decline surfaces shifts to the left (negative) as predicted above in FIG. 6.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

We claim:

1. A prosthetic/orthotic ankle-foot system comprising:
 a foot member;
 a shaft secured to the foot member for serving as an axis of rotation for the ankle-foot system;
 a support arm rotatably secured to the shaft;
 a first bumper interposed between the support arm and the foot member for maintaining and/or returning the support arm to a neutral position relative to the foot member;
 a first cam rotatably secured to the shaft;
 a second bumper interposed between the first cam and the foot member;
 a second cam rotatably secured to the support arm for engagement with the first cam;
 an upper housing movably secured to the support arm; and
 a link pivotally secured to both the upper housing and the second cam so that when the upper housing is moved toward the support arm, the second cam rotates downward into contact with the first cam, with dorsiflexion of the ankle-foot system causing rotation of the first cam and compression of the second bumper.

2. The system of claim 1 further comprising:
 an elongated bolt secured to the support arm, the upper housing being slidingly received on the bolt; and
 a compression member interposed between the upper housing and the support arm to resist movement of the upper housing toward the support arm.

3. The system of claim 2 wherein the compression member comprises a spring received on the bolt.

4. The system of claim 2 further comprising a spacer associated with one of the upper housing and the support arm and interposed therebetween to limit motion of the upper housing toward the support arm.

5. The system of claim 2 wherein the second cam has a circular configuration and is eccentrically mounted to the support arm.

6. The system of claim 2 wherein the upper housing is configured for attachment to a prosthetic pylon.

7. The system of claim 2 wherein the second bumper is relatively stiffer than the first bumper.

8. The system of claim 2 wherein the first cam has a first radius of curvature and the second cam has a second radius of curvature and the ratio of the first radius of curvature to the second radius of curvature is from 2:1 to 10:1.

9. The system of claim 8 wherein the ratio is 4:1.

* * * * *

UNITED STATES PATENT AND TRADEMARK OFFICE
CERTIFICATE OF CORRECTION

PATENT NO. : 8,597,369 B2  
APPLICATION NO. : 12/311818  
DATED : December 3, 2013  
INVENTOR(S) : Hansen et al.

Page 1 of 1

It is certified that error appears in the above-identified patent and that said Letters Patent is hereby corrected as shown below:

IN THE SPECIFICATION:

Column 1, Line 29 – "The inventions relates" should be changed to --The inventions relate--

Column 1, Lines 30 and 32 – "prosthesic" should be --prosthetic--

Column 4, Lines 26 and 38 – "prosthetic prosthetic" should be --prosthetic--

Column 4, Line 49 – "eveness" should be --evenness--

Column 8, Line 48 – "cave" should be --curve--

Column 9, Lines 5-7 – "FIG 11A shows the device in a loaded state. FIG 11B shows the device in an unloaded state." should read --FIG 11A shows the device in an unloaded state. FIG 11B shows the device in a loaded state.--

Column 13, Lines 61-62 – "beselected" should be --be selected--

Signed and Sealed this  
Twenty-seventh Day of May, 2014

Michelle K. Lee  
*Deputy Director of the United States Patent and Trademark Office*